United States Patent [19]

Abood

[11] Patent Number: 4,966,916
[45] Date of Patent: Oct. 30, 1990

[54] AGONISTS AND ANTAGONISTS TO NICOTINE AS SMOKING DETERRENTS

[76] Inventor: Leo G. Abood, 45 Crandon Way, Rochester, N.Y. 14618

[21] Appl. No.: 325,746

[22] Filed: Mar. 20, 1989

Related U.S. Application Data

[62] Division of Ser. No. 14,018, Feb. 12, 1987.

[51] Int. Cl.$^5$ ............................................. A61K 31/24
[52] U.S. Cl. .................................................... 514/534
[58] Field of Search ......................................... 514/534

Primary Examiner—Stanley J. Friedman
Attorney, Agent, or Firm—Wells & White

[57] ABSTRACT

Agonists and antagonists to nicotine are used as smoking deterrents.

The nicotinic *antagonists* have the following structural requirements:
  (1) Aromatic, cycloalkyl, and heterocyclic carbamic acid esters of di- and trialkylaminoalkyl alcohols.
  (2) Aromatic, cycloalkyl, and heterocyclic thiocarbamic acid esters of di- and trialkylaminoalkyl alcohols.
  (3) Aromatic, cycloalkyl, and heterocyclic carboxylic acid esters of di- and trialkylaminoalkyl alcohols.
  (4) Aromatic, cycloalkyl, and heterocyclic carboxylic acid esters of heterocyclic amino alcohols.
  (5) Lobelia alkaloids: lobeline, lobelanine, and lobelanidine.

The nicotinic *agonists* (nicotine-like) have the following structural requirements:
  (1) methylcarbamic acid esters of di- and trialkylaminoalkyl alcohols.
  (2) methylthiocarbamic acid esters of di- and trialkylaminoalkyl alcohols.

12 Claims, 1 Drawing Sheet

AGONISTS AND ANTAGONISTS TO NICOTINE AS SMOKING DETERRENTS

This is a division of application Ser. No. 07/014,018, filed Feb. 12, 1987.

BACKGROUND OF THE INVENTION

The field of the invention is tobacco and antismoking products (deterrents) and the present invention is particularly concerned with agonists and antagonists to nicotine.

The state of the art of tobacco smoking deterrents may be ascertained by reference to U.S. Pat. Nos. 4,276,890 and 4,311,691 of FICHERA and U.S. Pat. No. 4,579,858 of FERNOE et al, the disclosures of which are incorporated herein by reference.

Fernoe et al are aware of the prior art nicotine containing chewing gums as disclosed in U.S. Pat. Nos. 865,026; 940,521; 3,877,468; 3,901,248 and 3,845,217 and state that it seems particularly difficult to find other smoking substitutes equivalent to or as effective as these nicotine containing chewing gums. U.S. Pat. No. 4,579,858 discloses a smoking substitute composition for application directly into the nose, consisting essentially of an aqueous solution of nicotine or a physiologically acceptable acid addition salt thereof, having a pH value of 2 to 6, containing 10 to 0.5% w/v of nicotine calculated as the free base, containing a nasally-acceptable thickening agent, having a viscosity not less than 100 centipose, and having about 0.5 to 5 mg nicotine per every 0.05 to 0.5 ml thereof and a method of diminishing the desire of a subject to smoke, which comprises the step of administering to the subject intranasally this smoking substitute composition.

The patents of Fichera disclose that the approach used by Fernoe et al has the difficultly that a physiological dependence upon nicotine remains and that until this dependence is overcome, the opportunity to resume smoking is very high. U.S. Pat. No. 4,311,691 defines a composition for inhibiting tobacco smoking comprising a gamma pyrone and an inert physiologically acceptable carrier capable of providing sustained release of the gamma pyrone in the mouth over a time period of at least ten (10) minutes, in unit dosage form containing from 20 mg to 300 mg of gamma pyrone per unit dose and a chewing gum composition for inhibiting tobacco smoking comprising a chewing gum base having particulate ethyl maltol distributed uniformly throughout, providing 100 mg to 300 mg ethyl maltol per stick of gum.

U.S. Pat. No. 4,276,890 defines the method of inhibiting tobacco smoking of smokers without physiological symptoms of nicotine withdrawal comprising smoking while awake during the waking hours of the day and administering to such a smoker 500 mg to 1500 mg total daily dose of ethyl maltol or maltol as a gamma pyrone divided into several incremental doses during the waking hours of the day, each incremental dose being retained in the smoker's mouth and released therein over a period of at least 10 minutes, for at least about 5 to 10 days, for a total of about 20 to 30 days or at least until there results either of a gradual decrease in the number of cigarettes smoked and the length of time they are smoked or until such point as the lowered tobacco consumption rate becomes obvious.

Fichera has contributed the discovery that the administration of maltol or ethyl maltol at appropriate dosage levels and rates, significantly reduces the tobacco consumption of habitual smokers.

SUMMARY OF THE INVENTION

Applicant has discovered compounds and compositions which are agonists and antagonists to nicotine and therefore are useful as smoking deterents.

The nicotinic agonists and antagonists described in this invention are useful in treating the smoking habit. An agonist, such as dimethylaminoethylmethylcarbamate or methylcarbamylcholine, being pharmacologically similar to nicotine, substitute for nicotine at the receptors. Since they are readily metabolized by esterases and resemble the endogenous neurotransmitter, acetylcholine, the agonists are less habit forming.

The antagonists, on the other hand, are prescribed for the treatment of the tobacco habit by virtue of their ability to displace and compete with nicotine at the receptors, thereby preventing the pharmacologic effects of nicotine both on the peripheral and central nervous system.

These nicotine agonists and antagonists are capable of preventing the seizures, prostration, elevated blood pressure, and mortality resulting when various doses of nicotine are administered systemically or intraven-tricularly to rats.

The compounds exhibit specificity for nicotinic receptors as determined by their ability to compete with $^3$H-nicotine and $^3$H-methylcarbamylcholine for binding to rat brain membranes. The binding affinity of the compounds for the nicotinic receptors showed an excellent correlation with the pharmacologic potency of the antagonists.

The compounds are useful for counteracting the toxic effects of nicotine and related substances. The substances are useful for counteracting the cardiovascular and behavioral effects of nicotine and related substances.

Those compounds which are methylcarbamyl esters of dialkylaminoalkyl alcohols are nicotinic agonists, i.e., act similarly to nicotine in their cardiovascular, autonomic, and psychotropic action. An example is methylcarbamylcholine.

The nicotinic antagonists have the following structural requirements:
 (1) Aromatic, cycloalkyl, and heterocyclic carbamic acid esters of di- and trialkylaminoalkyl alcohols.
 (2) Aromatic, cycloalkyl, and heterocyclic thiocarbamic acid esters of di- and trialkylaminoalkyl alcohols.
 (3) Aromatic, cycloalkyl, and heterocyclic carboxylic acid esters of di- and trialkylaminoalkyl alcohols.
 (4) Aromatic, cycloalkyl, and heterocyclic carboxylic acid esters of heterocyclic amino alcohols.
 (5) Lobelia alkaloids: lobeline, lobelanine, and lobelanidine.

The nicotinic agonists (nicotine-like) have the following structural requirements:
 (1) Methylcarbamic acid esters of di- and trialkylaminoalkyl alcohols.
 (2) methylthiocarbamic acid esters of di- and trialkylaminoalkyl alcohols.

The compounds of the present invention can be administered according to the methods and compositions disclosed in U.S. Pat. Nos. 4,276,890, 4,311,691 and 4,579,858.

A unit dosage of 1 mg to 100 mg is advantageous and this dosage is administered three times a day. When the agonists and antagonists are admistered in chewing gum, a stick of gum contains 1 mg to 100 mg of the antagonist or agonist.

Figure 1:
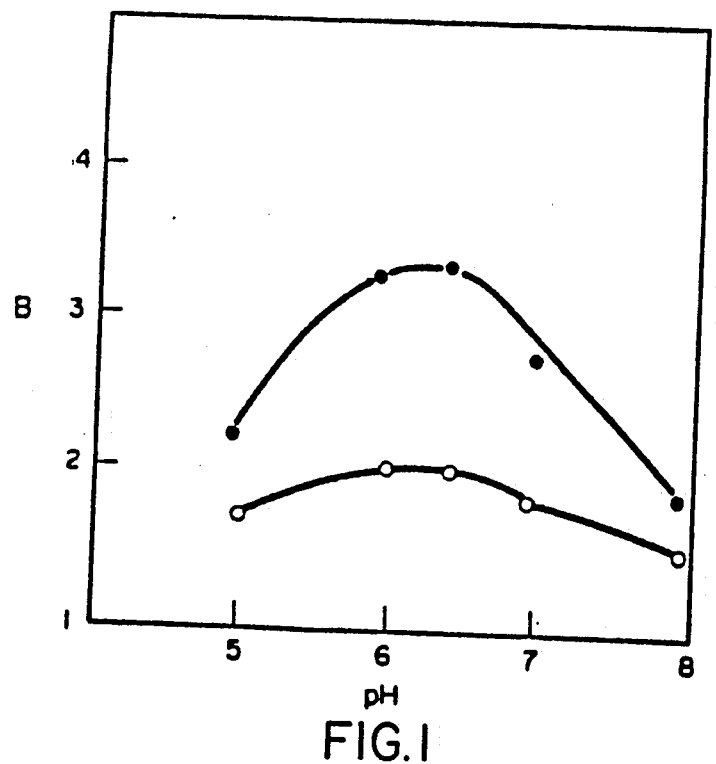
FIG. 1 is a pH curve for $^3$H-MCC and $^3$H-nicotine wherein:
the open dots=$^3$H-nicotine; the solid dots=$^3$H-MCC.
B=moles bound $\times 10^{-14}$.

The plot represents a study from three separate examples with coefficient of variation of the $K_d$ and $B_{max}$ values being under 8%. A 1000-fold excess of unlabeled ligand was used at each concentration of radioligand to obtain specific binding. B=amount bound and F=concentration of free $^3$H-MCC.

DESCRIPTION OF THE PREFERRED EMBODIMENTS

One of the agonists of the present invention is a new radioligand, [$^3$H]-methylcarbamyl choline and it has been used as an agonist at the nicotinic cholinergic and nicotine-like binding sites in rat brain membranes. A Scatchard analysis with the radioligand yielded a $K_d$ of $1.1 \times 10^{-9}$M and a $B_{max}$ of $4.0 \times 10^{-14}$ moles/mg protein which compares with a lower affinity site for $(-)0[^3H]$-nicotine having a $K_d$ of $3 \times 10^{-9}$M and a $B_{max}$ of $2 \times 10^{-14}$ moles/mg. Comparable values for the $K_d$ were obtained from a Hill plot and from calculations based on rate constants for association and dissociation. A comparison of the binding affinity of various nicotine analogues, nicotinic cholinergic agents and other neurotropic agents revealed a close similarity between the two radioligands, with the exception that quaternization of nicotine or carbamate esters increased affinity by at least an order of magnitude with [$^3$H]-methylcarbamyl choline and resulted in a comparable decrease in affinity with [$^3$H]-nicotine as the ligand. The binding of [$^3$H]-methylcarbamyl choline, like [$^3$H]-nicotine, was not displaceable by muscarinic cholinergic antagonists. It was concluded that although [$^3$H]-methylcarbamyl choline and [$^3$H]-nicotine bind to a common receptor in the brain, the functional and chemical characteristics of the receptor(s) differ in some respects from peripheral nicotinic cholinergic receptors.

In the course of evaluating the structure-activity relationships of the [$^3$H]-nicotine binding sites to rat brain membranes and purified receptor, it was observed that carbamylcholine and substituted carbamate esters of choline exhibited a relatively high affinity for the nicotine site. At a concentration of $10^{-9}$M S-$(-)$-[$^3$H]-nicotine, N-methylcarbamyl choline had an IC$_{50}$ value of $8 \times 10^{-9}$M as compared to a value of $2 \times 10^{-9}$M for unlabeled nicotine. Since carbamate esters of choline are considerably more stable than acetylcholine, an evaluation was undertaken with [$^3$H]-methylcarbamyl choline of high radioactive specific activity to determine its similarity to the [$^3$H]-nicotine and [$^3$H]-acetylcholine binding sites in rat brain membranes. A number of studies with [$^3$H]-acetylcholine, prepared enzymatically with [$^3$H]-acetic acid, have alluded to the similarity in the receptor binding characteristics of the two ligands.

The present evaluation demonstrates the effectiveness of [$^3$H]-methylcarbamyl choline ([$^3$H]-MCC) as a ligand for use as an agonist at the nicotine-like and nicotinic cholinergic binding sites in brain tissue.

EXAMPLE 1

Synthesis Of DMAE Methylcarbamate And MCC

To 0.05 moles of dimethylaminoethanol in 100 ml of dry toluene was added 0.07 moles of methylisocyanate, and the mixture was refluxed for 16 hours. After removal of the solvent in vacuo, the viscous liquid was taken up in 25 ml of CHCl$_3$ and extracted with H$_2$O. Upon removal of the CHCl$_3$, a white oily product was obtained and the final product was recovered after distillation in vacuo at 1 mm and a temperature of 135° C. The yield was 85%.

An infrared analysis of DMAE methylcarbamate yielded the following bands:
1730, 1540, 1385, 1100, 960, 995 790 cm$^{-1}$ Methylcarbamylcholine was prepared by adding 0.012 moles of methyl iodide to 0.010 moles of DMAE methylcarbamate in 50 ml acetone and allowing the reaction to proceed overnight at room temperature. The white crystalline material was filtered, washed with 50 ml of ethyl ether, and dried. The yield was 98%. Analysis by mass spectroscopy yielded the following fragment with % relative abundance:
58 (100%), 142 (27%), 28 (21%), 57 (12%), 71 (8%),
42 (8%), 30 (7%), 56 (6%), 59 (6%), 44 (6%)

[$^3$H]-MCC was prepared by New England Nuclear by quaternization of DMAE methylcarbamate with [$^3$H]-CH$_3$I. The purity of the [$^3$H]-MCC was verified by HPLC.

Measurement Of [$^3$H]-MCC And [$^3$H]-nicotine Binding

The procedure for preparation of rat brain membranes and for measuring specific [$^3$H]-MCC and [$^3$H]-nicotine binding is described by ABOOD et al in Neurochem. Res 10, 260 (1985). Membranes were obtained from whole rat brain after homogenization in 30 volumes of 0.05M NaPO$_4$, pH 7.0, and centrifugation at 50,000$\times$g for 30 minutes. To a 2 ml polypropylene tube was added 2 mg membrane protein along with various concentrations of either [$^3$H]-MCC (specific activity=80 Ci/mmole) or $(-)$-[$^3$H]-nicotine (New England Nuclear, specific activity=75 Ci/mmole) with or without various concentrations of unlabeled nicotine, nicotine analogues, carbamate esters and other agents, in a final volume of 1.2 ml 0.05M NaPO$_4$, pH 7.0. The relationship of pH to the binding of the two ligands was determined with 0.05M NaPO$_4$ buffer. All assays were performed in triplicate. After incubating in an ice bath (0°–4°) for 30 minutes, the tubes were centrifuged in an Eppendorf centrifuge for 2 minutes and the pellet washed twice by filling the tubes with buffer and aspirating. The bottom of the tubes were then cut off (animal nail clipper) and counted by liquid scintillation.

Psychotropic Evaluation Of Various Agents

The psychotropic action of the various agents was determined by administering various doses into the fourth ventricle through chronically implanted cannulae, as described by Abood et al, Neurosci. Biochem. 5 479 (1981). A dose of 4 nmoles of $(-)$-nicotine in 1 $\mu$l resulted in prostration of all four limbs, while 2 nmoles (IC$_{50}$) produced prostration in the hind limbs and some weakness in the forelimbs.

RESULTS

Comparison Of pH Curve Of $^3$H-MCC And $^3$H-nicotine Binding

The pH curves for both $^3$H-MCC and $^3$H-nicotine binding had a pH optimum around 6.5 (FIG. 1). Although the shape of the curves were similar, the change in pH on either side of the optimum was considerably greater for $^3$H-MCC

Scatchard Analysis Of [$^3$H]-MCC Binding

Figure 2:
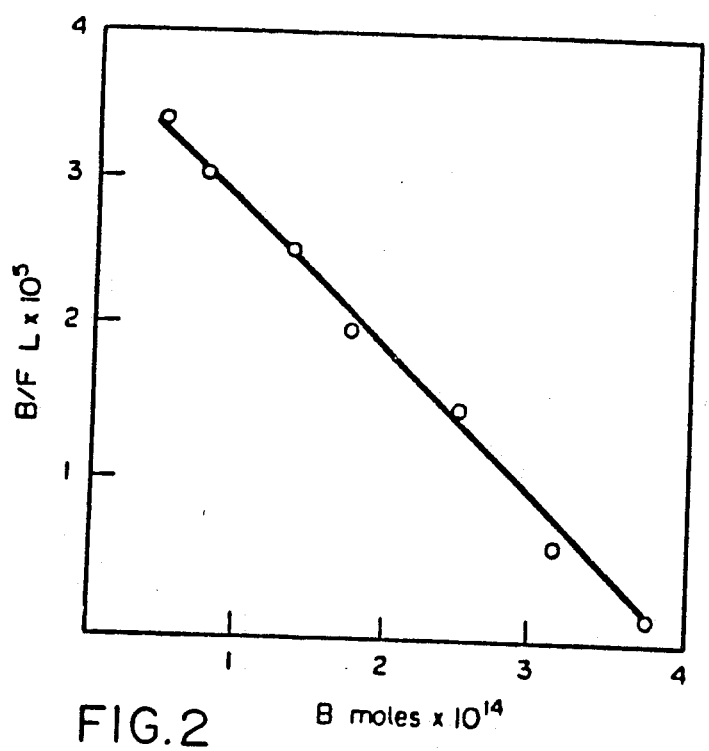
FIG. 2 is a Scatchard plot of [$^3$H]-MCC binding to rat brain membranes.

A Scatchard plot of [$^3$H]-MCC in the presence of unlabeled MCC was linear, yielding a $K_d$ of $1.1 \times 10^{-9}$M and a $B_{max}$ of $4.0 \times 10^{-14}$ moles/mg protein of whole rat brain membranes (FIG. 2). Replacement of unlabeled MCC with unlabeled (−)-nicotine also yielded a linear Scatchard with comparable $K_d$ and $B_{max}$ values. A Hill plot of the data [log (B/B-$B_{max}$ vs log F)] yielded a Hill binding constant of $9 \times 10^{-10}$M, which is in close agreement with the $K_d$ determined by Scatchard analysis.

$K_d$ Calculation From Rate Constants For Association And Dissociation

The rate constants for association for [$^3$H]-MCC binding to rat brain membranes was determined to be $3.0 \times 10^5$M$^{-1}$sec$^{-1}$; and for the dissociation $1.0 \times 10^{-3}$ sec$^{-1}$. The $K_d$, calculated from the ratios of the rate constants, was $3.3 \times 10^{-9}$M, a value which is in close agreement with that obtained by Scatchard analysis.

Comparison Of Various Agents In Competition With [$^3$H]-MCC And [$^3$H]-nicotine A variety of nicotine and cholinergic agents were compared for their ability to compete with [$^3$H]-MCC and [$^3$H]-nicotine binding to rat brain membranes (Table 1). At a concentration of 1 nM of [$^3$H]-nicotine, unlabeled (−) and (+)-nicotine had IC$_{50}$ values of $3 \times 10^{-9}$ and $1 \times 10^{-8}$M, respectively. With either radioligand, increasing the alkyl chain length on the pyrrolidine N resulted in 3-fold decrease with the N'-ethyl and a 200-fold decrease in affinity with the N'-propyl analogues of nicotine The affinity of N'-nicotonium was about 3 orders of magnitude less than (−)-nicotine with both radioligands. Comparable affinities with both radioligands were observed with the various carbamate esters, MCC having an affinity approaching that of (−)-nicotine. The $K_d$ value for acetylcholine was $5 \times 10^{-5}$M while that of hexamethonium, α-bungarotoxin, QNB and atropine was greater than $1 \times 10^{-4}$M.

TABLE 1

| PROCEDURE | DATA |
|---|---|
| Scatchard analysis | $K_d = 1.1 \times 10^{-9}$M |
|  | $B_{max} = 4.0 \times 10^{-14}$ moles/mg protein |
| Hill Pot | $K_d = 9 \times 10^{-10}$M |
| Rate Constants | $3.3 \times 10^{-9}$M |

$K_d$ determination by various analytic procedures.

Phychotropic Action Of Various Agents

The various agents were compared for their ability to induce prostration following administration into the rat fourth ventricle (Table 2). The (−)-enantiomer of nicotine was 20 times more effective than the (+)-enantiomer and 10, 40 and 50 times more potent than the N'-ethyl, N'-propyl, and nicotonium analogues, respectively Among the carbamate esters, MCC had 1/5 the potency of (−)-nicotine, while the others were relatively weak or inactive. The remainder of the agents, including acetylcholine, were inactive.

TABLE 2

|  | [$^3$H]-nicotine IC$_{50}$ M | [$^3$H]-MCC IC$_{50}$ M | Prostration EC$_{50}$ |
|---|---|---|---|
| (−)-nicotine | $3 \times 10^{-9}$ | $8 \times 10^{-9}$ | 2 |
| (+)-nicotine | $1 \times 10^{-8}$ | $9 \times 10^{-8}$ | 40 |
| N'-methyl nicotonium | $7 \times 10^{-6}$ | $4 \times 10^{-6}$ | 100 |
| N'-ethyl nornicotine | $3 \times 10^{-8}$ | $1 \times 10^{-7}$ | 20 |
| N'-propyl nornicotine | $6 \times 10^{-7}$ | $1 \times 10^{-6}$ | 80 |
| DMAE methylcarbamate | $5 \times 10^{-7}$ | $8 \times 10^{-7}$ | 300 |
| MCC | $8 \times 10^{-9}$ | $6 \times 10^{-9}$ | 10 |
| DMAE carbamate | $1 \times 10^{-5}$ | $1 \times 10^{-5}$ | >300 |
| carbamylcholine | $4 \times 10^{-7}$ | $1 \times 10^{-6}$ | 100 |
| acetylcholine | $6 \times 10^{-5}$ | $5 \times 10^{-6}$ | >100 |
| hexamethonium | $>1 \times 10^{-4}$ | $>1 \times 10^{-4}$ | IA |
| α-bungarotoxin | $>1 \times 10^{-4}$ | $>1 \times 10^{-4}$ | IA |
| QNB | $>1 \times 10^{-4}$ | $>1 \times 10^{-4}$ | IA |
| atropine | $>1 \times 10^{-4}$ | $>1 \times 10^{-4}$ | IA |

Comparison of IC$_{50}$ values for binding of various agents using [$^3$H]-nicotine and [$^3$H]-MCC as radioligands.

To determine psychotropic potency expressed as EC$_{50}$, at least 6 rats were used for every agent. DMAE=dimethylaminoethyl; QMB=3-quinuclidinyl benzilate. The IC$_{50}$ values were determined from plots of various concentrations of agents. EC$_{50}$ values were based on data from 6 rats. IA=inactive.

DISCUSSION

The present example has demonstrated that the receptor binding characteristics of [$^3$H]-MCC to rat brain are similar to those of [$^3$H]-nicotine; however, the Scatchard plot for [$^3$H]-MCC was linear while that for [$^3$H]-nicotine was biphasic. A similar $K_d$ was derived from dissociation-dissociation rate constants and from a Hill plot. The lower affinity site for [$^3$H]-nicotine had a $K_d$ of $3 \times 10^{-9}$M and $B_{max}$ of $1 \times 10^{-14}$ moles/mg membrane protein which compares favorably with the values for [$^3$H]-MCC. With [$^3$H]-nicotine, a higher affinity site with a $K_d$ of $2 \times 10^{-10}$M and $B_{max}$ of $0.5 \times 10^{-14}$ moles/mg was not seen with [$^3$H]-MCC. Although [$^3$H]-acetylcholine also appears to have similar binding characteristics to [$^3$H]-nicotine, [$^3$H]-MCC affords the advantages that it is chemically more stable and is more readily prepared. Another similarity between $^3$H-MCC and $^3$H-nicotine binding was the pH curve with an optimum of 6.5. A major difference between the two ligands is that [$^3$H]-acetylcholine, but not [$^3$H]-MCC binding, is displaceable by low concentrations of muscarinic antagonists When muscarinic agonists, such as [$^3$H]-oxotremorine-M disclosed by Birdsall et al in Mol. Pharmacol. 14, 723 (1978) and [$^3$H]-cis methyldioxolane disclosed by EHLERT et al in Life Sci. 26, 961 (1980) are employed as radioligands IC$_{50}$ values are obtainable with muscarinic antagonists in the nanomolar range. Since MCC is closely related to carbamylcholine, which is a muscarinic agonist and readily binds to the muscarinic cholinergic receptor, this finding was unexpected.

Although the relative binding affinity of a variety of nicotine analogues and other agents is similar with both radioligands, there is one striking difference. With either radioligand, quaternization of the pyrrolidine N of nicotine reduces the affinity by 3 orders of magnitude; whereas, quaternization of the carbamate esters results in about a 50-fold increase in affinity (compare DMAE methylcarbamate with MCC). It is also noteworthy that the psychotropic potency following intraventricular administration decreases 50-fold with quaternization of nicotine, while increasing over 10-fold after quaternization of DMAE methyl carbamate. The diminished psychotropic potency of N'-methylnicotonium is anomalous in view of the fact that when administered systemically, it is more potent than nicotine in producing seizures and mortality in rats or mice. This difference in the central and peripheral action and receptor affinity of nicotine and N'-methyl nicotonium suggests a difference in the nature of the two receptors. Binding studies with [$^3$H]-nicotine indicate that there may be at least two, and possibly more, nicotinic sites in rat brain; whereas, with [$^3$H]-MCC only one site is evident, which is presumably similar to the lower affinity site for nicotine. The functional significance of the low and high affinity sites for nicotine is not known. Since 1-2 $\mu$l of a $10^{-3}$M solution of nicotine administered into the fourth ventricles is required to produce prostration, it appears likely that the lower affinity site is associated with the psychotropic response. Since MCC and other carbamate esters of alkylaminoalcohols are chemically similar to acetylcholine, it would appear that MCC is interacting with a nicotinic site in brain, while being virtually inactive at a muscarinic cholinergic site.

Insofar as the binding characteristics of [$^3$H]-nicotine resemble those of [$^3$H]-MCC, both ligands evidently bind to the same receptor. The extremely low affinity of acetylcholine [4 orders of magnitude less than (−)-nicotine and MCC] and its correlative lack of psychotropic activity, when supersaturating concentrations of acetylcholine are administered intraventricularly leave partly unexplained the functional and biochemical nature of the sites. A similar disparity between the binding affinity and function of acetylcholine has been observed in the Torpedo electric organ which exhibits both a low and high affinity site for the nicotine antagonist, $\alpha$-bungarotoxin as disclosed by Conti-Tronconi et al in Biochem. Biophys. Res. Comm. 107, 123 (1982). Presumably, occupancy of the low affinity site by acetylcholine activates the ionic channel while occupancy of the high affinity site leads to desensitization; so that a nicotinic antagonist may prevent channel activation without occupying the recognition site as disclosed by Conti-Tronconi et al in Ann. Rev. Biochem. 51, 491 (1982). It is possible that either the higher affinity site involves a desensitized cholinergic receptor or that MCC and nicotine function as agonists at a high affinity recognition site whose relationship to acetylcholine remains obscure.

EXAMPLE 2

The present example discloses the synthesis and pharmacology of a number of carbamytes, cycloalkyl, and aryl esters of choline and other aminoalkyl alcohols with high affinity for the nicotinic binding site and which are effective antagonists to the psychotropic and other pharmacologic effects of nicotine.

There are multiple binding sites for (−)-nicotine in brain membranes. In addition to a high and low affinity binding site, there appears to be an allosteric site responsive to both (+)- or (−)-nicotine. The site exhibits positive cooperativity to both nicotine enantiomers when either (+)- or (−)-$^3$H-nicotine is used as the ligand.

METHODS

Measurement Of $^3$H-nicotine And $^3$H-MCC Binding

The procedure for preparation of rat brain membranes and for measuring specific $^3$H-nicotine and $^3$H-MCC binding is disclosed in Example 1. Membranes were obtained from whole rat brain after homogenization in 30 volumes of 0.05 M NaPO$_4$, pH 7.5, and centrifugation at 50,000$\times$g for 30 min. To a 2 ml polypropylene tube was added 2-3 mg membrane protein along with various concentrations of either $^3$H-MCC (specific activity=80 Ci/mmole) or (−)-$^3$H-nicotine (New England Nuclear, specific activity=75 Ci/mmole) with or without various concentrations of unlabeled nicotine, nicotine analogues, carbamate esters, and other agents, in a final volume of 1.2 ml 0.05 M NaPO$_4$ buffer containing 0.1 M NaCl at pH 7.5, or 8.5 in the case of (+)-$^3$H-nicotine. All assays were performed in triplicate. After incubating in an ice bath (0°-4°) for 30 min., the tubes were centrifuged in an Eppendorf centrifuge for 2 min. and the pellet washed twice by filling the tubes with buffer and aspirating. The bottom of the tubes was then cut off (animal nail clipper) and counted by liquid scintillation.

Pharmacologic Measurements

The psychotropic action of the agents was determined by assessing their ability, when administered intraventricularly (i.v.c.), to produce prostration (agonists) or prevent the nicotine-induced prostration (antagonists) by the procedure described in Example 1. The agents were administered into cannulae chronically implanted into the fourth ventricle of Sprague-Dawley male rats (200-250 g), in 1 $\mu$l volumes. A typical prostration response, occurring within 1-3 sec. following the injection of 2 nmoles of nicotine, generally involved all four limbs with body and neck muscles. Antagonism was determined by administering the test agent 1 min. prior to giving 2 nmoles of nicotine. Antagonism was also determined by measuring an agent's ability to prevent nicotine-induced seizures. The test agent was administered intraperitoneally (i.p.) 7 min. prior to the administration of 1.5 mg/kg nicotine i.p. A third method was to determine a test agent's ability to prevent lethality produced by 3 mg/kg nicotine i.p.

Arterial blood pressure was determined by means of a Gould Statham P23ID pressure transducer attached to the right femoral artery of rats anesthetized with 60 mg/kg sodium pentothal i.p. and connected to a polygraph. Various doses of test agent were administered 1 min. prior to the administration of a dose of nicotine (0.05 mg/kg) which resulted in a 42±20 mm Hg elevation of systolic blood pressure. The mean dose of a test agent necessary to completely block the hypertensive action of nicotine was determined.

RESULTS

Comparison Of Various Ester Agonists With $^3$H-nicotine And $^3$H-MCC Binding And Their Psychotropic Potency The various esters were compared for their ability to compete with $^3$H-nicotine and $^3$H-MCC binding to rat brain membranes, utilizing a concentration of $1\times10^{-9}$ M of each radioligand, which yielded an IC$_{50}$ value for nicotine of $2\times10^{-9}$ M and $6\times10^{-9}$ M for $^3$H-MCC. TMAE carbamate (carbamylcholine) had an IC$_{50}$ of $4\times10^{-7}$ M and $1\times10^{-6}$ for $^3$H-nicotine and $^3$H-MCC, respectively, whereas the corresponding DMAE derivative had a value of $1 \times 10^{-5}$ M with either radioligand. The most potent agent was TMAE methylcarbamate (methylcarbamyl choline) with an $IC_{50}$ value of $8 \times 10^{-9}$ M and $6 \times 10^{-9}$, compared to a value of $5 \times 10^{-7}$ M and $8 \times 10^{-7}$ for the two radioligands, respectively, for the DMAE analogue. No difference was noted in the $IC_{50}$ values between TMAE acetate (acetylcholine), TMAE succinate (succinylcholine), and their corresponding DMAE analogues, all having values of about $5 \times 10^{-5}$ M with either radioligand. The one exception was acetylcholine which had a 10-fold greater affinity with $^3$H-MCC than with $^3$H-nicotine.

Comparison Of Various Ester Antagonists For Binding And Blockade Of Prostration

Among the various esters, TMAE Benzoate was the most effective compound in blocking nicotine-induced prostration when both compounds were administered into the fourth ventricle of rats; next in effectiveness and of comparable activity were TMAE phenylcarbamate, TMAE phenylthiocarbamate, TMAE phenylacetate, and DMAE nicotinate. The quaternary esters were generally 10-fold more potent than the tertiary analogues, both with respect to their binding affinity and psychotropic action. The most potent of the compounds tested was the natural alkaloid, α-lobeline, which exhibited an even greater affinity than (−)-nicotine for the receptor and blocked the nicotine-induced prostration with a dose of 10 nmoles i.v.c. Other agents exhibiting some binding affinity were procaine and 9-aminotetrahydroacridine. The other agents listed, including cocaine and atropine, were inactive.

Antagonism Of Various Esters To Nicotine-induced Seizures

At a dose of 1.5 mg/kg nicotine intraperitoneally, rats exhibited prostration followed by tremors, fasciculations, cyanosis and labored breathing, and myoclonic seizures as shown in Table 5 which follows. When the rats were given 20 mg/kg TMAE benzoate or TMAE cyclohexylcarboxylate 7 min. prior to nicotine, there was a 78% blockade of seizure activity. At a dose of 25 mg/kg DMAE benzoate or DMAE cyclohexylcarboxylate, about half of the rats exhibited seizures. Both TMAE phenylcarbamate and 3-quinuclidinyl benzoate afforded almost complete protection. It should be noted that muscle weakness, some tremors, and a slower respiratory rate persisted in all animals despite the antagonist. At a dose of 5 mg/kg, α-lobeline afforded complete protection against seizures. No significant behavioral effects were observed with any of the esters alone.

Protection By Various Agents Against Nicotine Mortality In Rats

At a dose of 5 mg/kg i.p., α-lobeline resulted in a 75% reduction of the mortality produced by 3 mg/kg nicotine i.p. in rats. A dose of 25 mg/kg TMAE benzoate, TMAE cyclohexylcarboxylate, TMAE phenylcarbamate, TMAE phenylthiocarbamate, and 3-quinuclidinyl benzoate resulted in 63, 66, 50, 63 and 50% protection, respectively. Atropine was ineffective.

Antagonism Of Hypertensive Action Of Nicotine

The agents were tested for their ability to completely reverse a 25% increase in systolic blood pressure following a dose of 0.05 mg of nicotine given intravenously to anesthetized rats as shown in Table 7 which follows. The most effective agent was α-lobeline at a dose of 0.2 mg/kg followed by TMAE benzoate and TMAE cyclohexylcarboxylate at 1.5 mg/kg. At higher doses, ranging from 5-10 mg/kg, all the other esters tested were also effective.

Behavioral Effects Of Agents

The behavioral effects of the various agents administered i.v.c. were assessed either alone or in combination with nicotine to determine possible antagonism. When 20 nmoles of nicotine (10 μl) was administered i.v.c., there immediately ensued a prostration involving all four limbs and lasting 2-4 min. At 500 times this dose, carbamylcholine produced weakness in all limbs and head muscles, while DMAE carbamate had only a similar effect at 100 times the dose of nicotine. The most potent of the esters was methylcarbamylcholine which produced a prostration lasting over 20 min; but unlike the response to nicotine, the rats seemed somewhat paralyzed and unable to move their heads or limbs. At a dose of 500 nmoles, dimethylaminomethylcarbamate produced moderate weakness in the hindlimbs and head. The remainder of the compound tested alone were either inactive or had only a slight effect. All of the active compounds including nicotine produced deep diaphragmatic breathing and a decreased respiratory rate.

When 100 nmoles of benzoylcholine was administered 1 min prior to giving 20 nmoles of nicotine, the prostration response did not occur. The choline ester of benzoic acid was 5 times as effective as the DMAE ester. Procaine and cocaine, which are local anesthetics, both effectively block nicotine-induced prostration.

DISCUSSION

Example 2 demonstrates that (1) a number of newly synthesized and other esters of aminoalkyl and aminocycloalkyl alcohols and aromatic acids, and (2) α-lobeline are effective antagonists to the psychotropic and peripheral actions of nicotine and other nicotinic agonists. The most effective antagonist in blocking the prostration, seizures, and mortality following nicotine administration in rats was α-lobeline. Among the various esters of various alkylaminoalcohols, benzoylcholine was the most effective antagonist. Both antagonists also exhibited a very high affinity for brain nicotine receptors using either (−)-$^3$H-nicotine or $^3$H-methylcarbamylcholine as ligands. When the phenyl group of benzoylcholine was substituted with phenylalkyl, naphthoyl or phenylcarbamyl, the antagonistic potency was diminished. Replacement of the choline moiety by quinuclidinyl, piperidyl, or pyrrolidyl diminished antagonistic potency.

A series of carbamyl and alkyl esters of tertiary amino alcohols serving as agonists to the nicotine receptor, quaternization of N resulted in about a 20-fold increase in receptor affinity and a marked increase in pharmacologic potency. A similar increase in receptor affinity and antagonist potency was observed with the present series of esters acting as antagonists.

A number of miscellaneous alkoloids and esters were found to be antagonists, including procaine, a local anesthetic, and 9-aminotetrahydroacridine, an anticholinesterase. Other local anesthetics, such as cocaine and lidocaine and anticholinesterases, such as physostigmin and prostigmin are inactive.

A comparison of the chemical structures of the nicotine-like compounds with the carbamates with respect to their action on prostration reveals significant differences in the two classes of compounds. Both nicotine and 3-dimethylaminopyridine, which are arylamines, are agonists; whereas aryl esters of aminoalcohols, such as DMAE nicotinate and benzoylcholine, are antagonistic to the nicotine-induced prostration; while alkyl esters of aminoalcohols are agonists. Another striking difference is that within the series of arylamines related to nicotine, quaternization of the N'-nitrogen decreases binding affinity by 3 orders of magnitude and a virtual loss of psychotropic action, whereas in the series of alkyl esters quaternization of the aminoalcohol results in about a 50-fold increase in affinity for the nicotine receptor and a corresponding increase in psychotropic potency.

Although α-lobeline has been reported by Sollman in "A Manual of Pharmacology", 7th edition, Saunders, Philadelphia, 1948, p. 352 to suppress the desire for tobacco, the pharmacologic relationship of this natural alkaloid to nicotine is obscure. Included among the pharmacologic effects of α-lobeline are its hypertensive action resulting from the stimulation of the carotid body as disclosed by Heymans et al in L. Arch. int. Pharmacodyn, 1932, 43, 86, broncio-construction as disclosed by Cambar et al in Arch. int. Pharmacodyn. 1969, 177, 1, and bronchoarrythmia as disclosed by Korczyn et al in Arch. int. Pharmacodyn. 1969, 182, 370. It has been suggested that the cardiovascular effects are both parasympathetic (muscarinic) and sympathetic. It has been generally assumed that α-lobeline is a ganglionic stimulant resembling nicotine. The present example indicates that the alkaloid is also acting as an antagonist at nicotine receptors both centrally and peripherally.

It has been reported that N-methylcarbamylcholine was about 5 times more potent than acetylcholine or carbamylcholine in contracting rectus abdominus muscle and 40 times less potent than carbamylcholine in contracting guinea pig ileum. It has been reported that N-methylcarbamylcholine and related carbamates are metabolized by a rat liver microsomal system requiring NADP (nicotinamide adenine dinucleotide) as a coenzyme.

A number of di- and trialkylaminoalkyl N-arylcarbamates have been synthesized and shown to have herbicidal and anthelminthic as well as antileukemic and hypotensive properties.

TABLE $^3$H-nicotine And $^3$H-MCC Binding Of Various Agents And Their Ability To Produce Prostration

|  | $^3$H-Nicotine Binding IC$_{50}$ M | $^3$H-MCC Binding IC$_{50}$ M | Prostration EC$_{50}$ nmoles |
|---|---|---|---|
| s-(−)-nicotine | $2 \cdot 10^{-9}$ | $8 \times 10^{-9}$ | 2 |
| N'-methyl nicotinium | $7 \times 10^{-6}$ | $4 \times 10^{-6}$ | 100 |
| N'-ethyl nornicotine | $3 \times 10^{-8}$ | $1 \times 10^{-7}$ | 20 |
| N'-propyl nornicotine | $6 \times 10^{-7}$ | $1 \times 10^{-6}$ | 80 |
| DMAE carbamate | $1 \times 10^{-5}$ | $1 \times 10^{-5}$ | 400 |
| TMAE carbamate | $4 \times 10^{-7}$ | $1 \times 10^{-6}$ | 100 |
| DMAE methylcarbamate | $5 \times 10^{-7}$ | $8 \times 10^{-7}$ | 300 |
| TMAE methylcarbamate | $8 \times 10^{-9}$ | $6 \times 10^{-9}$ | 10 |
| DMAP methylcarbamate | $2 \times 10^{-7}$ | $5 \times 10^{-8}$ | 100 |
| DMAE acetate | $5 \times 10^{-5}$ | $5 \times 10^{-5}$ | >1000 |
| TMAE acetate (acetylcholine) | $6 \times 10^{-5}$ | $5 \times 10^{-6}$ | 300 |
| DMAE succinate | $5 \times 10^{-5}$ | $6 \times 10^{-5}$ | 1000 |
| TMAE succinate butyrythiocholin | $8 \times 10^{-7}$ | $7 \times 10^{-7}$ | 50 |
| cytisine | $6 \times 10^{-9}$ | $1 \times 10^{-10}$ | 2 |

DMAE = 2-dimethylaminoethyl
TMAE = 2-trimethylaminoethyl
DMAP = 3-dimethylaminopropyl

TABLE 4

$^3$H-nicotine And $^3$H-MCC Binding Of Various Agents And Their Efficacy In Blocking Nicotine-induced Prostration

|  | $^3$H-Nicotine Binding IC$_{50}$ M | $^3$H-MCC Binding IC$_{50}$ M | Blockade of Prostration EC$_{50}$ nmoles |
|---|---|---|---|
| *DMAE benzoate | $1 \times 10^{-6}$ |  | 100 |
| *TMAE benzoate | $8 \times 10^{-8}$ | $4 \times 10^{-8}$ | 10 |
| DMAE cyclohexylcarboxylate | $2 \times 10^{-6}$ | $4 \times 10^{-6}$ | 100 |
| TMAE cyclohexylcarboxylate | $8 \times 10^{-8}$ | $5 \times 10^{-8}$ | 10 |
| DMAE phenylcarbamate | $1 \times 10^{-4}$ | $1 \times 10^{-4}$ | IA |
| TMAE phenylcarbamate | $6 \times 10^{-6}$ | $8 \times 10^{-7}$ | 200 |
| DMAE phenylthiocarbamate | $7 \times 10^{-5}$ | $2 \times 10^{-5}$ |  |
| TMAE phenylthiocarbamate | $5 \times 10^{-7}$ | $5 \times 10^{-7}$ | 50 |
| *DMAE nicotinate | $2 \times 10^{-7}$ | $2 \times 10^{-7}$ | 50 |
| TMAE nicotinate |  |  |  |
| 3-Quinuclidinyl benzoate | $7 \times 10^{-6}$ | $6 \times 10^{-6}$ | 200 |
| 3-Quinuclidinyl methylcarbamate | $3 \times 10^{-6}$ | $2 \times 10^{-6}$ | 100 |
| DMAE phenylacetate | $7 \times 10^{-5}$ | $7 \times 10^{-6}$ |  |
| TMAE phenylacetate | $2 \times 10^{-6}$ | $3 \times 10^{-7}$ | 100 |
| DMAE napththoate | $8 \times 10^{-5}$ | $7 \times 10^{-5}$ |  |
| TMAE napththoate | $9 \times 10^{-6}$ | $5 \times 10^{-6}$ |  |
| N-methyl-3-piperdylbenzoate | $3 \times 10^{-5}$ | $2 \times 10^{-5}$ | 300 |
| N-benzylpiperidyl methylcarbamate | IA | IA |  |
| N-benzyl-4-piperdyl methylcarbamate | IA | IA | IA |
| *N-methyl-3-piperidyldiphenylacetate | IA | IA | IA |
| *atropine | IA | IA | IA |
| N-methyltetrahydropapavarine | $7 \times 10^{-5}$ | $8 \times 10^{-5}$ |  |
| *9-aminotetrahydroacridine | $2 \times 10^{-5}$ | $1 \times 10^{-5}$ | 200 |
| *procaine | $7 \times 10^{-5}$ | $3 \times 10^{-5}$ |  |
| *cocaine | $>1 \times 10^{-4}$ | $>1 \times 10^{-4}$ | IA |
| *α-lobeline | $5 \times 10^{-9}$ | $7 \times 10^{-10}$ | 10 |

TABLE 4-continued $^3$H-nicotine And $^3$H-MCC Binding Of Various Agents And
Their Efficacy In Blocking Nicotine-induced Prostration

|  | $^3$H-Nicotine Binding IC$_{50}$ M | $^3$H-MCC Binding IC$_{50}$ M | Blockade of Prostration EC$_{50}$ nmoles |
|---|---|---|---|
| *lobelanine | $1 \times 10^{-8}$ | $5 \times 10^{-9}$ | 25 |
| *lobelanidine | $2 \times 10^{-8}$ | $5 \times 10^{-9}$ | 25 |

DMAE = 2-dimethylaminoethyl
TMAE = 3-trimethylaminoethyl
IA = inactive
IC$_{50}$ = concentration inhibiting binding 50%
EC$_{50}$ = dose in nmoles producing 50% efficacy

TABLE 5

Antagonism Of Various Agents To Nicotine-induced
Seizures In Rats
The test agents were administered intraperitoneally
7 min. prior to 1.5 mg/kg nicotine Except as indicated, the
dose of all other agents was 25 mg/kg.

| Agent | Seizures | % Antagonism |
|---|---|---|
| Nicotine | 10/10 | — |
| +α-lobeline 5 mg/kg | ⅛ | 0/8 |
| +TMAE benzoate | ⅛ | 78 |
| +DMAE benzoate 50 mg/kg | 5/9 | 45 |
| DMAE cyclohexylcarboxylate 50 mg/kg | 4/8 | 50 |
| TMAE cyclohexylcarboxylate | ⅛ | 78 |
| +TMAE phenylcarbamate | 1/9 | 89 |
| +3-quinuclidinyl benzoate | 1/7 | 86 |
| +atropine | 6/6 | 0 |

TABLE 6

Protection Against Nicotine Mortality In Rats By
α-lobeline And Various Esters
Data are based on 10 rats given 25 mg/kg of test
agent followed by 3 mg/kg nicotine (neutralized with HCl)
5 min. later; both agents given i.p.

| Agent | Mortality | % Antagonism |
|---|---|---|
| (−)-nicotine 3 mg/kg | 8/10 | — |
| +α-lobeline 5 mg/kg | 2/10 | 75 |
| +TMAE benzoate | 3/10 | 63 |
| +TMAE cyclohexylcarbamate | 3/9 | 66 |
| +TMAE phenylcarbamate | 4/10 | 50 |
| +TMAE phenylthiocarbamate | 3/10 | 63 |
| +3-quinuclidinyl benzoate | 4/10 | 50 |
| +atropine 25 m/kg | | |

TABLE 7

Antagonism Of Hypertensive Action Of Nicotine By Various
Agents.
The dose (±s.d.) refers to that needed in mg/kg to
completely block a 42 ± 20 mm Hg elevation in systolic blood
pressure following the administration of 0.05 mg/kg nicotine i.v.

| Agent | Antagonistic dose |
|---|---|
| α-lobeline | 0.2 ± 0.05 |
| TMAE benzoate | 1.5 ± 0.3 |
| DMAE benzoate | 10.0 ± 25 |
| TMAE phenylcarbamate | 5.0 ± 1.0 |
| TMAE cyclohexylcarboxylate | 5.0 ± 1.5 |
| TMAE penylthiocarbamate | 4.0 ± 0.8 |
| 3-quinuclidinyl benzoate | 5.0 ± 1.2 |

EXAMPLE 3

DMAP methylcarbamate

To 0.05 moles of dimethylaminopropanol in 100 ml of dry toluene was added 0.07 moles of methylisocyante, and the mixture was refluxed for 16 hours. After removal of the solvent in vacuo, the viscous liquid was taken up in 2 ml of CHCl$_3$ and extracted with H$_2$O. Upon removal of the CHCl$_3$, a white oily product was obtained and the final product was recovered after distillation in vacuo at 5 mm and a temperature of 84° C. The yield was 60%.

An infared analysis of DMAP methylcarbamate yielded the following bands:
2990, 1730, 1560, cm$^{-1}$
Analysis by mass spectroscopy yielded the following:
160, 91, 70, 58

EXAMPLE 4

Quinuclidinol methylcarbamate

To 0.05 moles of 3-quinuclidinol dissolved in 100 ml of dry toluene was added to 0.07 moles of methylisocyanate and the mixture was refluxed for 8 hours. After removal of the solvent in vacuo, the mixture was taken up to 50 ml of H$_2$O and extracted twice with H$_2$O. After removal by CHCl$_3$, the yellow oily liquid was distilled in vacuo at 5 mm Hg and 130° C. The yield was.

An infrared analysis of quinuclidinol methylcarbamate yielded the following bands:
2985, 1730, 1530, 1265 cm$^{-1}$
Analysis by mass spectroscopy yielded the following:
184, 156, 58

EXAMPLE 5

DMAE And TMAE Phenylcarbamate

To 0.05 moles of dry dimethylaminoethanol in 100 ml of dry toluene was added 0.07 moles of phenylisocyanate, and the mixture was refluxed for 16 hours. After removal of the solvent in vacuo, the viscous liquid was taken up in 25 ml of CHCl$_3$ and extracted with H$_2$O. Upon removal of the CHC$_3$, a white oily product was obtained and the final product was recovered after distillation in vacuo at 5 mm at 145° C. The yield was 65%.

An infrared analysis of DMAE phenylcarbamate yielded the following bands:
1730, 1600 cm$^{-1}$
Analysis by mass spectroscopy yielded the following:
212, 164, 119

TMAE phenylcarbamate was prepared by adding 0.013 moles of methyl iodide to 0.010 moles of DMAE phenylcarbamate in 50 ml of acetone and allowing the reaction to proceed overnight at room temperature.

The white crystalline material was filtered, washed twice with 50 ml of ethyl ether, and dried. The yield was 90%.

EXAMPLE 6

DMAE And TMAE Phenylthiocarbamate

The conditions are the same as for DMAE and TMAE phenylcarbamate in Example 5 except that reflux was 8 hours. The product was recovered by distillation in vacuo at 5 mm and at 117° C. The yield was 58%.

An infrared analysis of DMAE phenylthiocarbamate yielded the following bands:
2990, 1725, 1550, 1225 cm$^{-1}$
Analysis by mass spectroscopy yielded the following: 219, 194, 93

EXAMPLE 7

DMAE And TMAE Naphthoate

To 0.05 moles of dry dimethylaminoethanol in 100 ml of dry methylene chloride at room temperature was added slowly with stirring over a period of 15 min. 0.05 ml of napththoyl chloride in 50 ml of methylene chloride. After another 30 min. the contents were extracted with $H_2O$ and the organic phase concentrated in vacuo. The final product was purified by distillation at 5 mm Hg and 176° C. The yield was 55%.

An infrared analysis of DMAE naphthoate yielded the following bands:
2980, 1750, 1595, 1240 cm$^{-1}$
Analysis by mass spectroscopy yielded the following: 199, 155, 127

TMAE naphthoate was prepared by adding 0.013 moles of methyl iodide to 0.010 moles of DMAE naphthoate in 50 ml of acetone and allowing the reaction to proceed overnight at room temperature. The white crystalline material was filtered, washed twice with 50 ml of ethyl ether and dried. The yield was 90%.

EXAMPLE 8

DMAE And TMAE Phenylacetate

To 0.05 moles of dry dimethylaminoethanol in 100 ml of dry methylene chloride at room temperature was added slowly with stirring over a period of 15 min. 0.05 ml of phenylacetyl chloride in 50 ml of methylene chloride. After another 30 min., the contents were extracted with $H_2O$ and the organic phase concentrated in vacuo. The final product was purified by distillation at 5 mm Hg and 168° C. The yield was 55%.

An infrared analysis of DMAE phenylacetate yielded the following bands:
2960, 1730, 1450, 1380 cm$^{-1}$
Analysis by mass spectroscopy yielded the following: 207, 163, 142

TMAE phenylacetate was prepared by adding 0.013 moles of methyl iodide to 0.010 moles of DMAE phenylacetate in 50 ml of acetone and allowing the reaction to proceed overnight at room temperature. The white crystalline material was filtered, washed twice with 50 ml of ethyl ether and dried. The yield was 90%.

EXAMPLE 9

3-Quinuclidinol Benzoate And N-methyl-3-quinuclidinyl Benzoate

To a mixture of 0.05 moles of 3-quinuclidinol in 100 ml of dry methylene chloride at room temperature was added slowly with stirring over a period of 15 min. 0.05 moles of benzoyl chloride in 50 ml of methylene chloride. After the reaction had proceeded an additional 30 min., the contents were extracted with $H_2O$ and the organic phase removed and concentrated in vacuo. The final product was purified by distillation at 5 mm Hg and 176° C. The yield was 40%.

An infrared analysis of 3-quinuclidinol benzoate yielded the following bands:
2950, 1730, 1600 cm$^{-1}$
Analysis by mass spectroscopy yielded the following: 227, 100, 137

N-methyl-3-quinuclidinyl benzoate was prepared by the addition of 0.013 moles of methyl iodide to 0.01 moles of 3-quinuclidyl benzoate.

EXAMPLE 10

DMAE And TMAE Cyclohexylcarboxylate

To 0.05 moles of dry dimethylaminoethanol in 100 ml of dry methylene chloride at room temperature was added slowly with stirring over a period of 15 min. 0.05 ml of cyclohexylcarboxyl chloride in 50 ml of methylene chloride. After another 30 min., the contents were extracted with $H_2O$ and the organic phase concentrated in vacuo. The final product was purified by distillation at 5 mm Hg and 176° C. The yield was 55%.

An infrared analysis of DMAE cyclohexylcarboxylate yielded the following bands:
2940, 1730, 1450, 1250, 1175
Analysis by mass spectroscopy yielded the following: 224, 170, 143, 97

TMAE cyclohexylcarboxylate was prepared by adding 0.013 moles of methyl iodide to 0.010 moles of DMAE cyclohexylcarboxylate in 50 ml of acetone and allowing the reaction to proceed overnight at room temperature. The white crystalline material was filtered, washed twice with 50 ml of ethyl ether and dried. The yield was 90%.

EXAMPLE 11

DMAE And TMAE Cyclopentylcarboxylate

To 0.05 moles of dry dimethylaminoethanol in 100 ml of dry methylene chloride at room temperature was added slowly with stirring over a period of 15 min. 0.05 ml of cyclopentylcarboxyl chloride in 50 ml of methylene chloride. After another 30 min., the contents were extracted with $H_2O$ and the organic phase concentrated in vacuo. The final product was purified by distillation at 5 mm Hg and 176° C. The yield was 55%.

An infrared analysis of DMAE cyclopentylcarboxylate yielded the following bands:
2940, 1730, 1450, 1170 cm$^{-1}$
Analysis by mass spectroscopy yielded the following: 197, 154, 140, 127

TMAE cyclopentylcarboxylate was prepared by adding 0.013 moles of methyl iodide to 0.010 moles of DMAE cyclopentyllcarboxylate in 50 ml of acetone and allowing the reaction to proceed overnight at room temperature. The white crystalline material was filtered, washed twice with 50 ml of ethyl ether and dried. The yield was 90%.

The following examples are the protocols for the use of nicotinic agonists and antagonists for treating the tobacco habit of humans.

EXAMPLE 12

To aid a chronic smoker in discontinuing the tobacco habit, a 25 mg capsule of dimethylaminoethyl methylcarbamate HCl is administered orally 3 times daily for a period of 5-8 weeks.

EXAMPLE 13

In order to counteract the effects of nicotine and, thereby, diminish the desire for tobacco, a 25 mg tablet or capsule of dimethylaminoethyl cyclohexylcarboxylate HCl is given orally 3 times daily for a period of 5-8 weeks.

EXAMPLE 14

In order to counteract the effects of nicotine and, thereby, diminish the desire for tobacco, a 25 mg tablet or capsule of 3-quinuclidinyl benzoate is given orally 3 times daily for a period of 5-8 weeks.

EXAMPLE 15

In order to counteract the effects of nicotine and, thereby, diminish the desire for tobacco, a 25 mg tablet or capsule of dimethylaminoethyl benzoate is given orally 3 times daily for a period of 5-8 weeks.

EXAMPLE 16

The nicotine antagonist, α-lobeline HCl is administered orally in 2 mg capsules or tablets 3 times daily to treat the tobacco habit.

EXAMPLE 17

The nicotinic antagonist, benzoyl choline is used to counteract the cardiovascular and gastrointestinal disturbances due to the effects of nicotine in tobacco. The protocol consists of administering 10 mg capsules or tablets of the hydrochloride salt of benzoyl choline 3 times daily to a human being with a smoking habit.

EXAMPLE 18

The nicotinic antagonist, choline ester of cyclohexylcarboxylic acid is used to counteract the cardiovascular and gastrointestinal disturbances due to the effects of nicotine in tobacco. The protocol consists of administering orally 10 mg capsules or tablets of the choline ester of cyclohexylcarboxylic acid 3 times daily to a human being with a smoking habit.

EXAMPLE 19

The nicotinic antagonist, α-lobeline, is used to counteract the cardiovascular and gastrointestinal disturbances due to the effects of nicotine in tobacco. The protocol consists of administering orally 10 mg capsules or tablets of the hydrochloride salt of α-choline 3 times daily to a human being with a smoking habit.

EXAMPLE 20

Example 1 of U.S. Pat. No. 4,276,890 is repeated with the substitution of methylcarbamyl choline for the maltol and ethyl maltol to form troches.

EXAMPLE 21

Example 2 of U.S. Pat. No. 4,276,890 is repeated with the substitution of methylcarbamyl choline for the ethyl maltol to sticks of chewing gum.

I claim:

1. A composition for inhibiting tobacco smoking comprising a nicotine antagonist dispersed in inert physiologically acceptable carrier in unit dosage form containing from 1 mg to 100 mg of said nicotine antagonist per unit dose, wherein said nicotine antagonist is selected from the group consisting of dimethylaminoethyl phenylthiocarbonate, trimethylaminoethyl phenylcarbamate, dimethylaminoethyl phenylthiocarbamate and trimethylaminoethyl phenylthiocarbamate.

2. A method of inhibiting tobacco smoking of smokers comprising administering to said smoker 3 mg to 300 mg total daily dose of a nicotine antagonist selected from the group consisting of dimethylaminoethyl phenylthiocarbocenate, trimethylaminoethyl phenylcarbamate, dimethylaminoethyl phenylthiocarbamate and trimethylaminoethyl phenylthiocarbamate.

3. A chewing gum composition for inhibiting tobacco smoking comprising a chewing gum base having a particulate nicotine antogonist distributed uniformly throughout, providing 1 mg to 100 mg of said nicotine antagonist per stick of gum, said nicotine antagonist selected from the group consisting of dimethylaminoethyl phenylthiocarbocenate, trimethylaminoethyl phenylcarbamate, dimethylaminoethyl phenylthiocarbamate and trimethylaminoethyl phenylthiocarbamate.

4. A method of inhibiting tobacco smoking of smokers comprising administering to said smoker 3 mg to 300 mg total daily dose of a nicotine antagonist selected from the group consisting of dimethylaminoethyl benzoate and trimethylaminoethyl benzoate.

5. The method of claim 4, wherein said nicotine antagonist is dimethylaminoethyl benzoate.

6. The method of claim 4, wherein said nicotine antagonist is trimethylaminoethyl benzoate.

7. A composition for inhibiting tobacco smoking comprising a nicotine antagonist dispersed in an inert physiologically acceptable carrier in unit dosage form containing from 1 mg to 100 mg of said nicotine antagonist per unit dose, wherein said nicotine antagonist is selected from the group consisting of dimethylaminoethyl benzoate and trimethylaminoethyl benzoate.

8. A chewing gum composition for inhibiting tobacco smoking comprising a chewing gum base having a particulate nicotine antagonist distributed uniformly throughout, providing 1 mg to 100 mg of said nicotine antagonist per stick of gum, said nicotine antagonist selected from the group consisting of dimethylaminoethyl benzoate and trimethylaminoethyl benzoate.

9. The composition of claim 7, wherein said nicotine antagonist is dimethylaminoethyl benzoate.

10. The composition of claim 7, wherein said nicotine antagonist is trimethylaminoethyl benzoate.

11. The composition of claim 8, wherein said nicotine antagonist is dimethylaminoethyl benzoate.

12. The composition of claim 8, wherein said nicotine antagonist is trimethylaminoethyl benzoate.

* * * * *